United States Patent [19]

Valcavi et al.

[11] Patent Number: 5,198,430
[45] Date of Patent: Mar. 30, 1993

[54] INCLUSION COMPLEXES WITH SILYBININ, THEIR PREPARATION AND PHARMACEUTICAL COMPOSITIONS CONTAINING THEM

[75] Inventors: Umberto Valcavi, Milan; Vincenzo Monterosso, Nova Milanese; Roberto Caponi; Enrico Bosone, both of Milan, all of Italy; Wilfried Wächter, Bergisch Gladbach, Fed. Rep. of Germany; Jozsef Szejtli, Budapest, Hungary

[73] Assignee: Istituto Biochimico Italiano Giovanni Lorenzini SpA, Milan, Italy

[21] Appl. No.: 593,933

[22] Filed: Oct. 9, 1990

[30] Foreign Application Priority Data

Oct. 9, 1989 [IT] Italy ......................................... 21962

[51] Int. Cl.$^5$ .................. A61K 31/685; A61K 31/70; C08B 37/16
[52] U.S. Cl. .......................................... 514/58; 536/103
[58] Field of Search ........................... 536/103; 514/58

[56] References Cited

U.S. PATENT DOCUMENTS 4,727,064 2/1988 Pitha ..................................... 536/103
4,826,963 5/1989 Stadler nee Szoke et al. ..... 536/103
4,834,985 5/1989 Elger et al. ........................... 424/488
4,869,904 9/1989 Uekama et al. ...................... 424/489

FOREIGN PATENT DOCUMENTS 209038 1/1987 European Pat. Off. .
2133405 7/1984 United Kingdom .

OTHER PUBLICATIONS

Chem. Pharm. Bull., No. 4, 1983, pp. 1350-1356; H. Sekikawa et al.: "Dissolution Behavior and Gastrointestinal Absorption of Dicumarol from Solid Dispersion Systems of Dicmarol-Polyvinylpyrrolidone and Dicumarol-β-Cyclodextrin".
Szejtli, "Cyclodextrin Technology", Kluwer Academic Publishers, London, England, 1988, p. 84.

Primary Examiner—Ronald W. Griffin
Attorney, Agent, or Firm—Armstrong & Kubovcik

[57] ABSTRACT

The invention relates to inclusion complexes of Silybinin with a cyclodextrin selected from the group consisting of α-, β- and γ-cyclodextrin and a suitable derivative thereof and to the method for the preparation thereof. The inclusion complexes of Silybinin showed a highly improved bioavailability in comparison to Silybinin which makes them particularly interesting in the treatment of various hepatotoxic conditions.

10 Claims, 11 Drawing Sheets

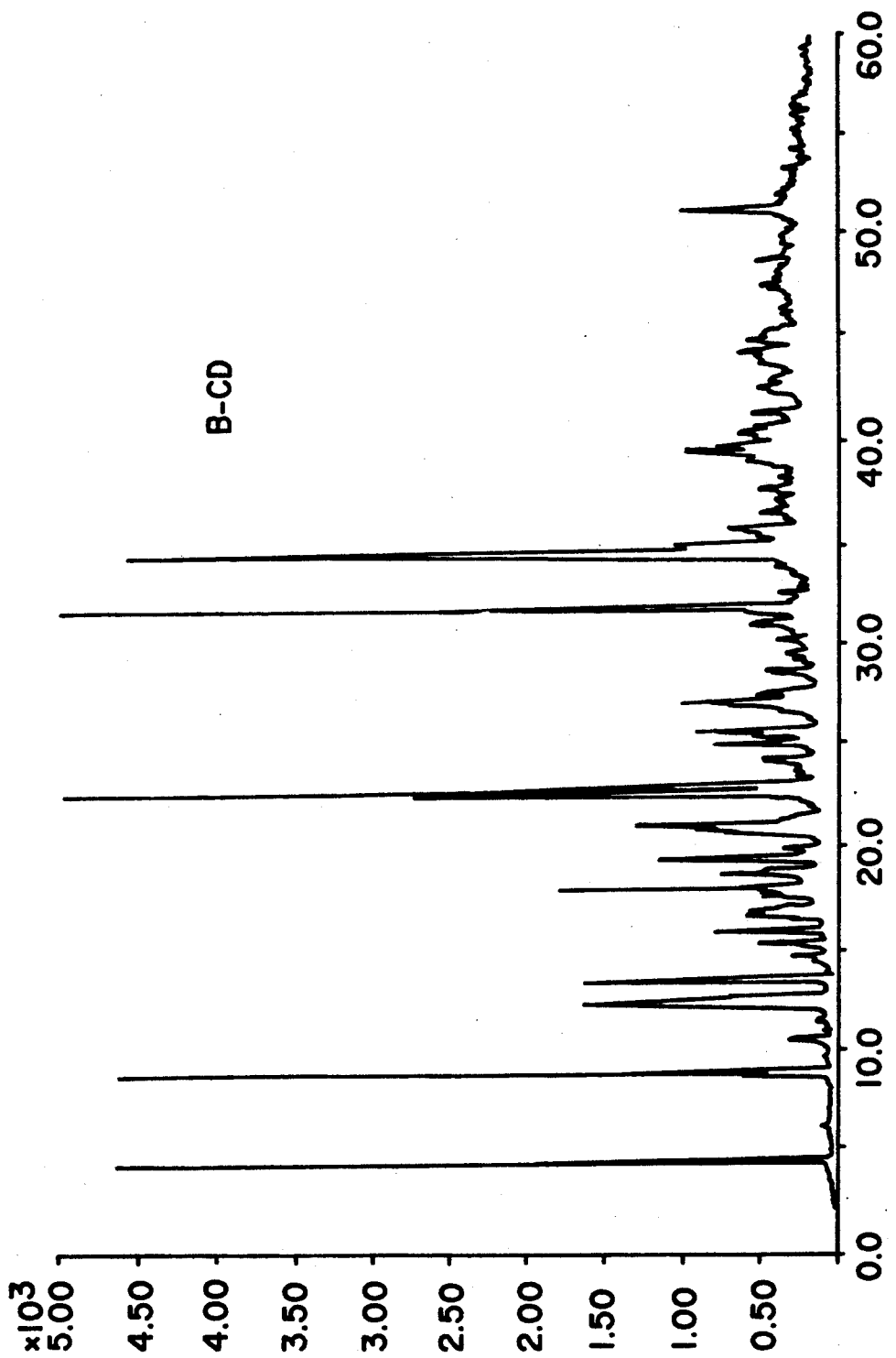

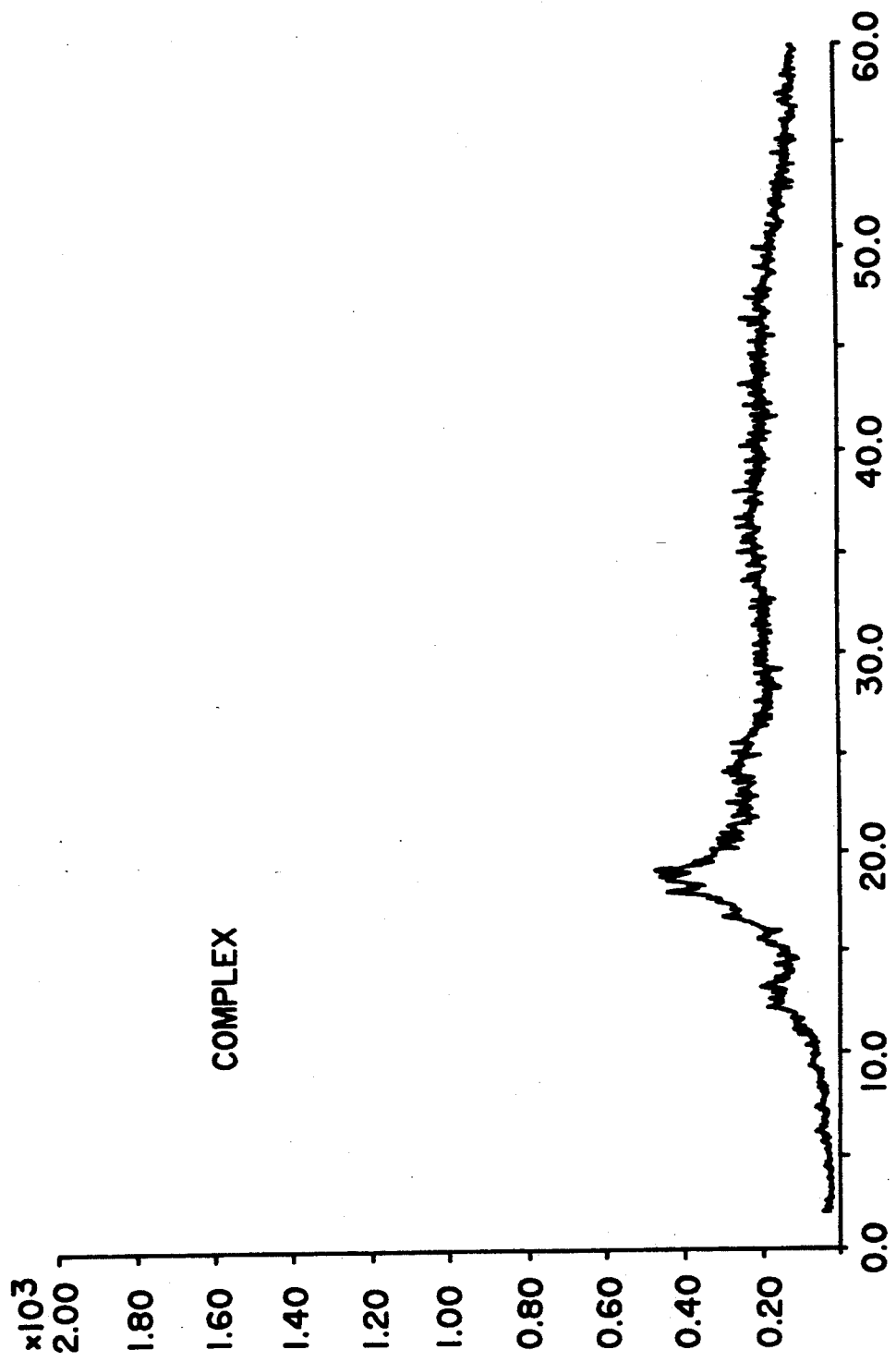
FIG.ID

INCLUSION COMPLEXES WITH SILYBININ, THEIR PREPARATION AND PHARMACEUTICAL COMPOSITIONS CONTAINING THEM

The object of the present invention relates to inclusion complexes of Silybinin with a cyclodextrin or with a derivative thereof, to a process for their preparation as well as to pharmaceutical compositions containing said inclusion complexes as active ingredients.

Silybinin is one of the isomers—more precisely it is the isomer therein present in the highest amount—which constitute Silymarin (or Silymarin group) and has the formula:

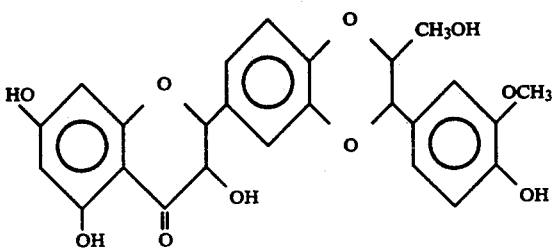

It may be obtained by extraction from the fruit of Carduus marianus, and is endowed with an interesting antihepatotoxic activity. The preparation of Silybinin is for example disclosed in DE-A-35 37 656.

Silybinin itself, formulated with suitable excipients in suitable ratios, shows an interesting antihepatotoxic activity which renders it of a particular interest in several pathological conditions.

It has been now found, and that constitutes the object of the present invention, that Silybinin, suitably treated with a cyclodextrin selected from the group consisting of $\alpha$-, $\beta$- and $\gamma$-cyclodextrin and a suitable derivative thereof, in particular the O—$C_1$-$C_4$-alkyl and hydroxy-$C_1$-$C_4$-alkyl derivatives forms a novel inclusion complex which compared to the Silybinin isomer shows an improved bioavailability.

A further object of the present invention is constituted by the process for the preparation of an inclusion complex of Silybinin with a cyclodextrin selected from the group consisting of $\alpha$-, $\beta$- and $\gamma$-cyclodextrin and a suitable derivative thereof.

A further object of the present invention is represented by the pharmaceutical compositions suitable for the oral administration which contain as active principle an inclusion complex of Silybinin with a cyclodextrin selected from the group consisting of $\alpha$-, $\beta$- and $\gamma$-cyclodextrin and a suitable derivative thereof. Preferably Silybinin having a HPLC titre on anhydrous higher than 90%, is used. Among $\alpha$-,$\beta$-and $\gamma$-cyclodextrin and the suitable derivatives thereof, $\beta$-cyclodextrin, hydroxypropyl-$\beta$-cyclodextrin, eptakis-2,6-O-dimethyl-$\beta$-cyclodextrin and eptakis-2,3,6-O-trimethyl-$\beta$-cyclodextrin are particularly preferred. More particularly, for the preparation of the inclusion complex of the present invention, Silybinin and cyclodextrin or its selected derivative, are mixed, optionally in warm conditions, at the Silybinin: cyclodextrin molar ratio of from 1:1 to 1:4, in an aqueous solution of a suitable organic solvent such as a di-$C_1$-$C_4$-alkyl or $C_5$-$C_7$-cycloalkyl ketone or an $C_1$-$C_4$-alkyl alcohol and therefrom the desired inclusion complex is obtained.

Suitable solvents among the ketones may be acetone, cyclohexanone, methylisobutylketone and diethylketone. Among the alcohols are suitable methyl, ethyl and isopropyl alcohol. Particularly preferred are methyl and ethyl alcohols.

More particularly an aqueous solution of an alcohol, such as for example methyl or ethyl alcohol, containing the desired components is made to react and then the product which forms is precipitated by cooling. In an alternative, the components are dissolved in the aqueous solution of the selected alcohol, the solution is concentrated by evaporation and submitted to lyophilization or dried by evaporating or spray drying.

According to a further process, which is encompassed within the scope of the present invention, the inclusion complex of the invention may be easily obtained by preparing a solution of Silybinin and cyclodextrin at a pH above 7, adjusting the pH to below 7 and isolating the complex formed. This process comprises suspending Silybinin in water and then adding to it a suitable base, preferably ammonium hydroxide, sodium or potassium hydroxide, until complete dissolution of Silybinin. To the so obtained solution, cyclodextrin is added, or its selected derivative, to such an extent to have the molar ratio Silybinin: cyclodextrin from 1:1 to 1:4. After a period of time, varying from 15 minutes to a few hours, the solution is evaporated or after having removed the majority of the base used, it is neutralized or acidified to a pH below 7, preferably 3 to 4, using a suitable acid, for example HCl, $H_3PO_4$, $H_2SO_4$. The complex is then isolated according to known techniques, for example by lyophilization. The solution of Silybinin and cyclodextrin can also be prepared by admixing them in water and continuing by adding a base as stated above.

The solubilization and the release rate of the complexes according to the invention are much higher as compared to Silybinin. An acceptable release rate is a premise for an useful absorption. The good absorption of the present complexes results in high Silybinin levels.

The inclusion complex of Silybinin with a cyclodextrin according to the present invention can be conveniently formulated in pharmaceutical compositions suitable for the oral administration, using excipients like anionic surfactants, such as sodium laurylsulphate, polyalcohols having molecular weight from 400 to 20,000, preferably from 1,500 to 3,000, simple and reticulate polyvinylpyrrolidones, cellulose and derivatives, such as hydroxypropylmethylcellulose, sodium carboxymethylcellulose and ethylcellulose.

The most preferred oral pharmaceutical forms are tablets, hard or soft gelatin capsules and granulated product in bags.

BRIEF DESCRIPTION OF THE DRAWINGS

FIGS. 1A, 1B, 1C and 1D show X-ray diagrams of Silybinin, a physical mixture of Silybinin with $\beta$-cyclodextrin, $\beta$-cyclodextrin and the complex of Example 1, respectively.

Figure 1A:
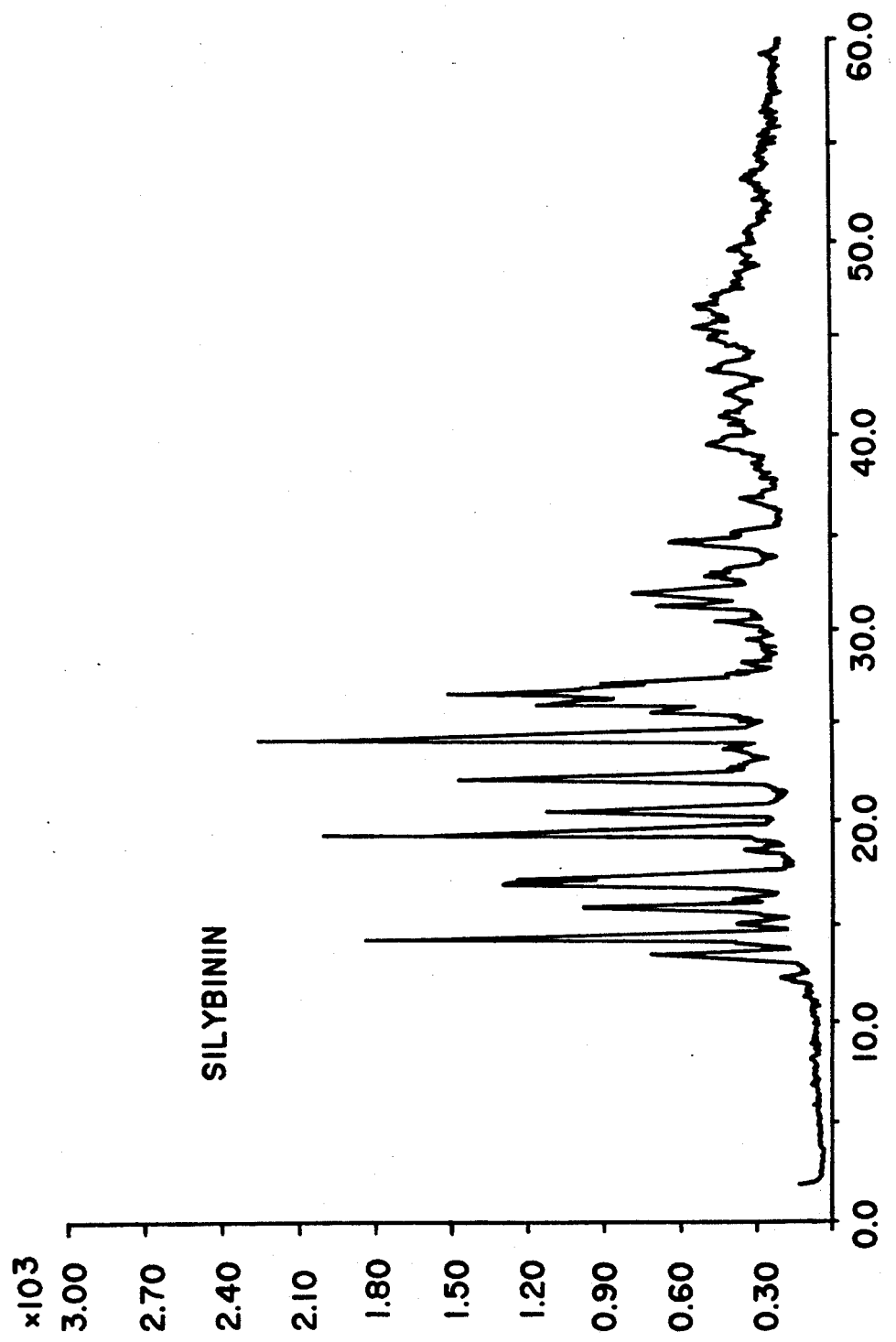
Figure 1B:
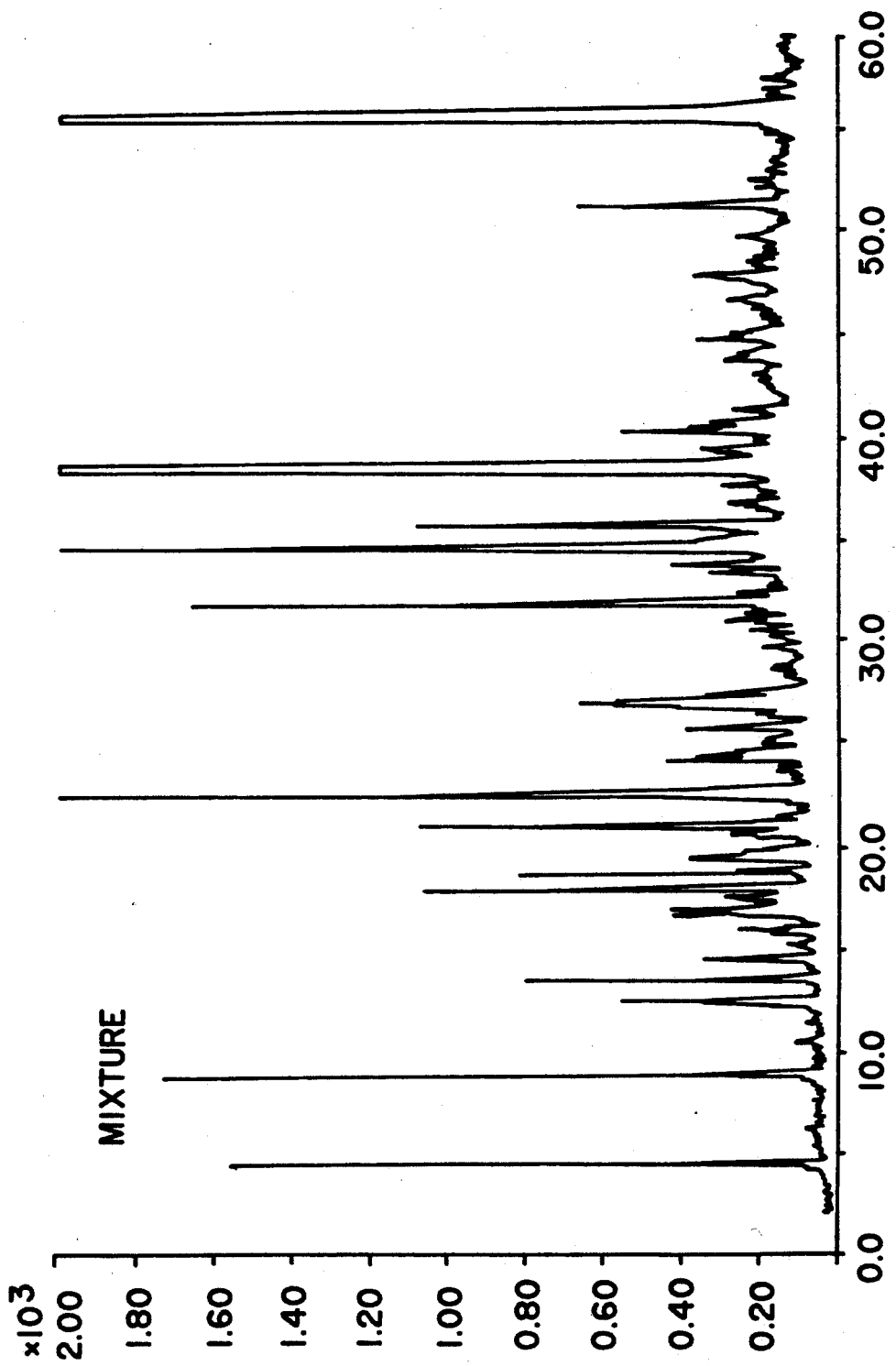

The following Examples are given with the purpose of illustrating the invention without limiting it.

EXAMPLE 1

Preparation of the Silybinin: β-cyclodextrin Inclusion Complex (Molar Ratio 1:1)

Grams 10 of Silybinin (titre 93%, 0.019 moles) are suspended in 200 ml deionized water and under magnetical stirring 75 ml 35% ammonium hydroxyde are dropped in 10 minutes therein. When the addition is completed 24.78 g β-cyclodextrin (Fischer 13%; 0.019 moles) are added thereto all at once. Stirring is maintained for a further 35 minutes then the water is distilled off in 15 minutes under vacuo at 50° C. The yellow solid which forms, is washed twice with 30 ml acetone and dried to give 24.6 g of a light yellow solid, soluble in water, which on X-ray analysis shows the characteristic peaks due to the Silybinin: β-cyclodextrin inclusion complex (1:1) (e.g. $2\theta = 18.8$) and melting point 250° C. UV (max) 287 nm (MeOH).

The inclusion complex according to the present invention shows a higher dissolution in comparison to the dissolution demonstrated, in the same experimental conditions, by either Silybinin and Silymarin.

Figure 8:
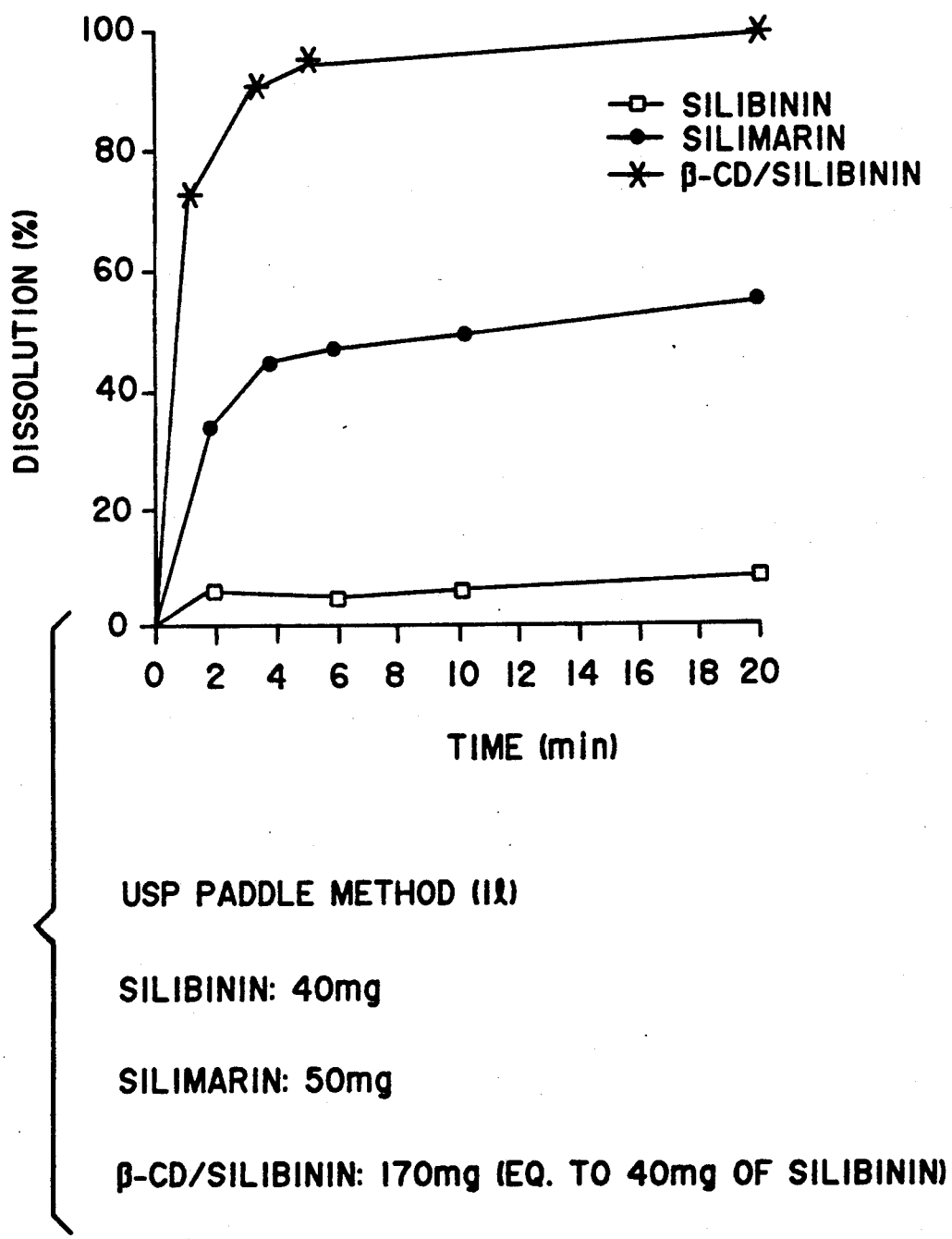
FIG. 8 shows dissolution curves of the complex Silybinin:β-cyclodextrin of Example 1, of Silybinin and of Silymarin dissolved in gastric juice at pH 6.8.

This characteristic is made evident by FIG. 8 where the dissolution curves of the complex Silybinin: β-cyclodextrin, prepared according to Example 1 (148 mg of complex corresponding to 40 mg of pure Silybinin), of Silybinin (40 mg) and of Silymarin dissolved in gastric juice at pH 6,8 are reported.

The evaluation has been carried out according to the USP paddle method and the determinations have been performed by UV in comparison to known standards.

The X-ray diffraction diagram of the inclusion complex according to Example 1 is characterized by the presence of some significant peaks (e.g. $2\theta = 18.8$) which cannot be revealed in the X-ray diffraction diagram of the powder formed by the mechanical mixture of the two components; furthermore in the X-ray diffraction diagram of the above mentioned inclusion complex are not present those peaks ($2\theta = 24.5$; 14.6; 32; 22.7) which are characteristics of the diffraction diagram of the mechanical mixture of the two components.

EXAMPLE 2

Preparation of the Silybinin: β-cyclodextrin Inclusion Complex (Molar Ratio 1:1)

Grams 10 of Silybinin (titre 93%, 0.019 moles) are suspended in 200 ml deionized water and under magnetical stirring 75 ml 35% ammonium hydroxide are dropped in 10 minutes therein. When the addition is completed 24.78 g β-cyclodextrin (Fischer 13%; 0.019 moles) are added thereto all at once. Stirring is maintained for a further 35 minutes then the gaseous ammonium excess is removed under vacuo, pH is adjusted to 7 adding 6N hydrochloric acid, it is lyophilized, washed twice with 30 ml each of acetone to give 26.2 g of a yellow solid (HPLC titre in Silybinin 24.7% t.a.) having spectrum characteristics as the product of the previous Example.

EXAMPLE 3

Preparation of the Silybinin: β-cyclodextrin Inclusion Complex (Molar Ratio 1:2)

Operation is carried out as described in the previous Examples using 35 g of pure Silybinin and 211.7 g β-cyclodextrin corresponding to 183.7 g on anhydrous. Grams 218 of the product having HPLC titre in Silybinin 15.41% and KF=2.5%, are obtained.

EXAMPLE 4

Preparation of the Silybinin γ-cyclodextrin Inclusion Complex (Molar Ratio 1:1)

Operation is carried out as described in Example 1 using 5.1 g γ-cyclodextrin having titre 98% and 2.04 g Silybinin having titre 91% corresponding to 1.857 g pure Silybinin. Grams 5.9 of Silybinin: γ-cyclodextrin inclusion complex (1:1) are obtained.

EXAMPLE 5

Preparation of the Silybinin: DIMEB (eptakis-2,6-O-dimethyl-β-cyclodextrin) Inclusion Complex (Molar Ratio 1:1)

Operation is carried out as described in Example 1 using 32.3 g of Silybinin having titre 93% and 82.4 g DIMEB. Grams 97.2 of Silybinin: eptakis-2,6-O-dimethyl-β-cyclodextrin inclusion complex (1:1) are obtained.

The products obtained as described in the previous Examples may be used for preparing pharmaceutical compositions by addition of suitable excipients and according to the operation described in the following Examples.

EXAMPLE 6

Preparation of Silybinin-β-cyclodextrin-Complex (Molar Ratio 1:2.75)

Grams 109.75 β-cyclodextrin (96,6 mmol) were dissolved in 600 ml of distilled water; 16.94 g of Silybinin (35 mmol) were added to the solution giving a suspension. About 75 ml of 1N sodium hydroxide solution was added dropwise over a period of 10 min with continuous stirring. Silybinin easily dissolved resulting in a yellow solution.

2N phosphoric acid solution was added to adjust the pH between 3.2–3.4 (about 100–105 ml of phosphoric acid is needed). The temperature of the solution during the dissolution and the neutralization process was kept below 20° C. by using an ice bath. The solution lost its colour at a pH below 5. The UV-spectra of the solution after 1:800 dilution with 50% (v/v) ethanol showed that Silybinin was present in unionized form in the solution. The slightly opalescent beige tone solution was filtered across a 04 glass filter. The solid complex was isolated from the clear solution by freeze drying.

Grams 140 of Silybinin-β-cyclodextrin complex was obtained. Active ingredient content: 12.1% (w/w) measured by UV-spectrophotometry. Loss on drying (at 105° C. under vacuo 2 h): 9.5% (w/w)

Release experiments with Silybinin, Silymarin and the complex of this Example were carried out according to USP XXII, paddle apparatus at pH 7.5 and 37° C. The experiments showed a 96% release (solubility) of the complex in contrast to 0% release of Silybinin and 53% total release of Silymarin corresponding to 37.1% Silybinin release.

EXAMPLE 7

Preparation of Silybinin-2,6-di-O-methyl-β-cyclodextrin-Complex (Molar Ratio 1:2.2)

The method of Example 6 was repeated except that 110 g 2,6-di-O-methyl-β-cyclodextrin (DIMEB; 82 mmol) and 18 g Silybinin (37 mmol) were used.

Grams 140 of Silybinin-DIMEB complex was obtained. Active ingredient content: 12.6% (w/w) measured by UV-spectrophotometry. Loss on drying (at 105° C. under vacuo 2 h): 5.0% (w/w).

EXAMPLE 8

Preparation of Silybinin-hydroxypropyl-β-cyclodextrin Complex (Molar Ratio 1:2.2)

Grams 100 hydroxypropyl-β-cyclodextrin (HP CD) 76 mmol. PS=3.0 (PS=average degree of substitution per cyclodextrin unit) was dissolved in 700 ml of water. Grams 17 Silybinin (35 mmol) was added, resulting in a suspension, approx. 70 ml of 1N sodium hydroxide was added dropwise to the solution over a period of 10 min. Further processing of the solution is identical with the preparation of DIMEB complex and 130 g of Silybinin-HPβCD complex was obtained.

Active ingredient content: 12.7% (w/w). Loss on drying (at 105° C. under vacuo 2 h): 7.0%.

X-ray analysis of the complexes of Examples 7 and 8.

Figure 2:
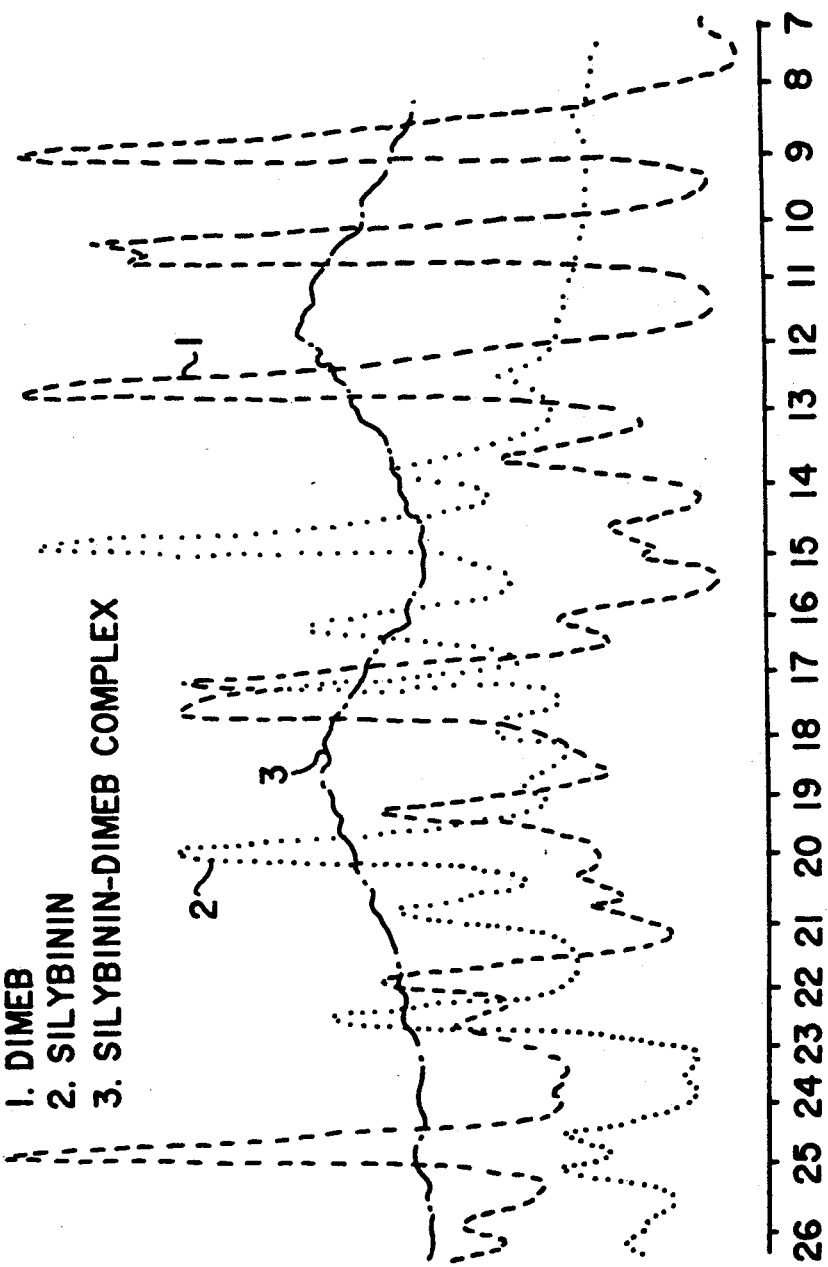
FIG. 2 shows the X-ray diffraction patterns of Silybinin, DIMEB and the complex of Example 7
Figure 3:
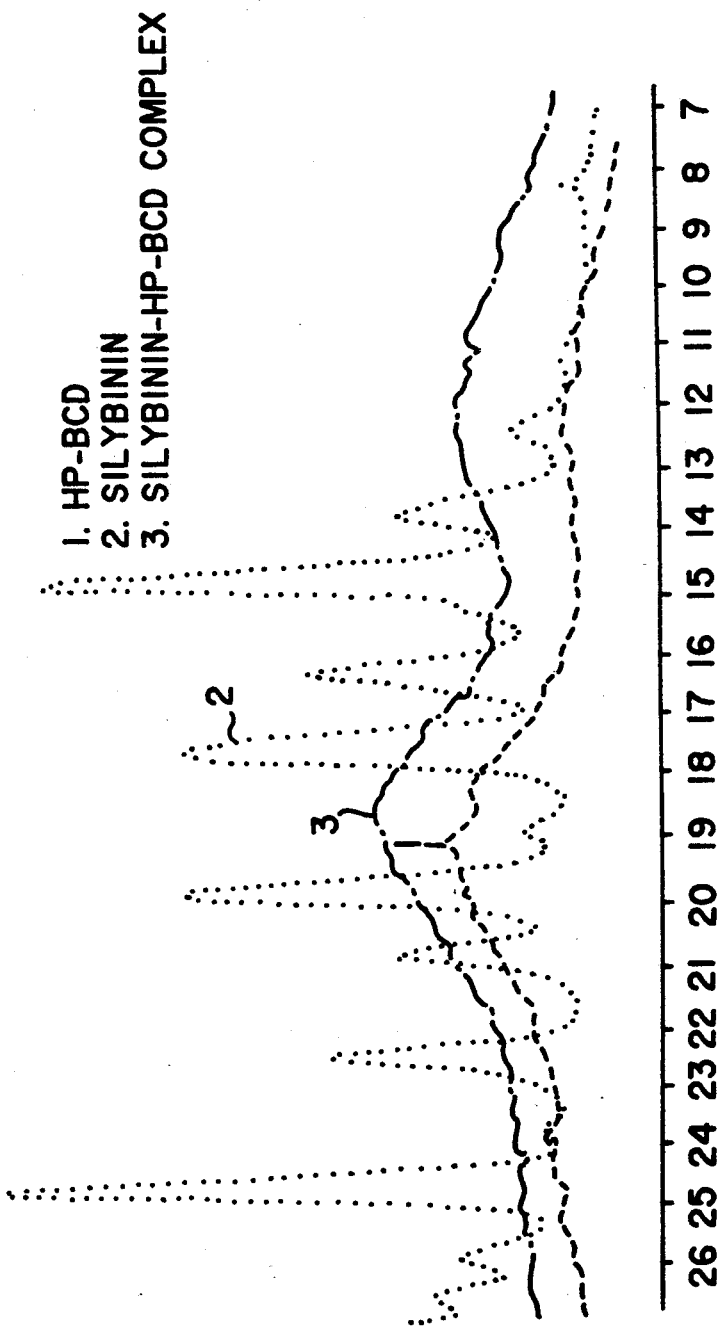
FIG. 3 shows the X-ray diffraction patterns of Silybinin, HP$\beta$CD and the complex of Example 8

X-ray power diffraction diagrams of pure Silybinin, DIMEB, HP-βCD and the complex samples were recorded on Philips powder diffractometer using Cu-K radiation. Comparing the X-ray patterns (FIGS. 2,3), the characteristic 2θ peaks of the crystalline Silybinin and DIMEB disappeared, the complexes showed a completely different structure in both cases.

Thermoanalytical Studies

Thermoanalytical investigations were carried out on a Du Pont 990 Thermal Analyser System. TG (Thermogravimetry) DTG (Differential TG) DSC (Differential Scanning Calorimetry) and TEA (Thermal Evolution Analysis) curves of the drug, as well as those of its mechanical mixtures with DIMEB and HP-βCD and the complexes were taken simultaneously.

Figure 4:
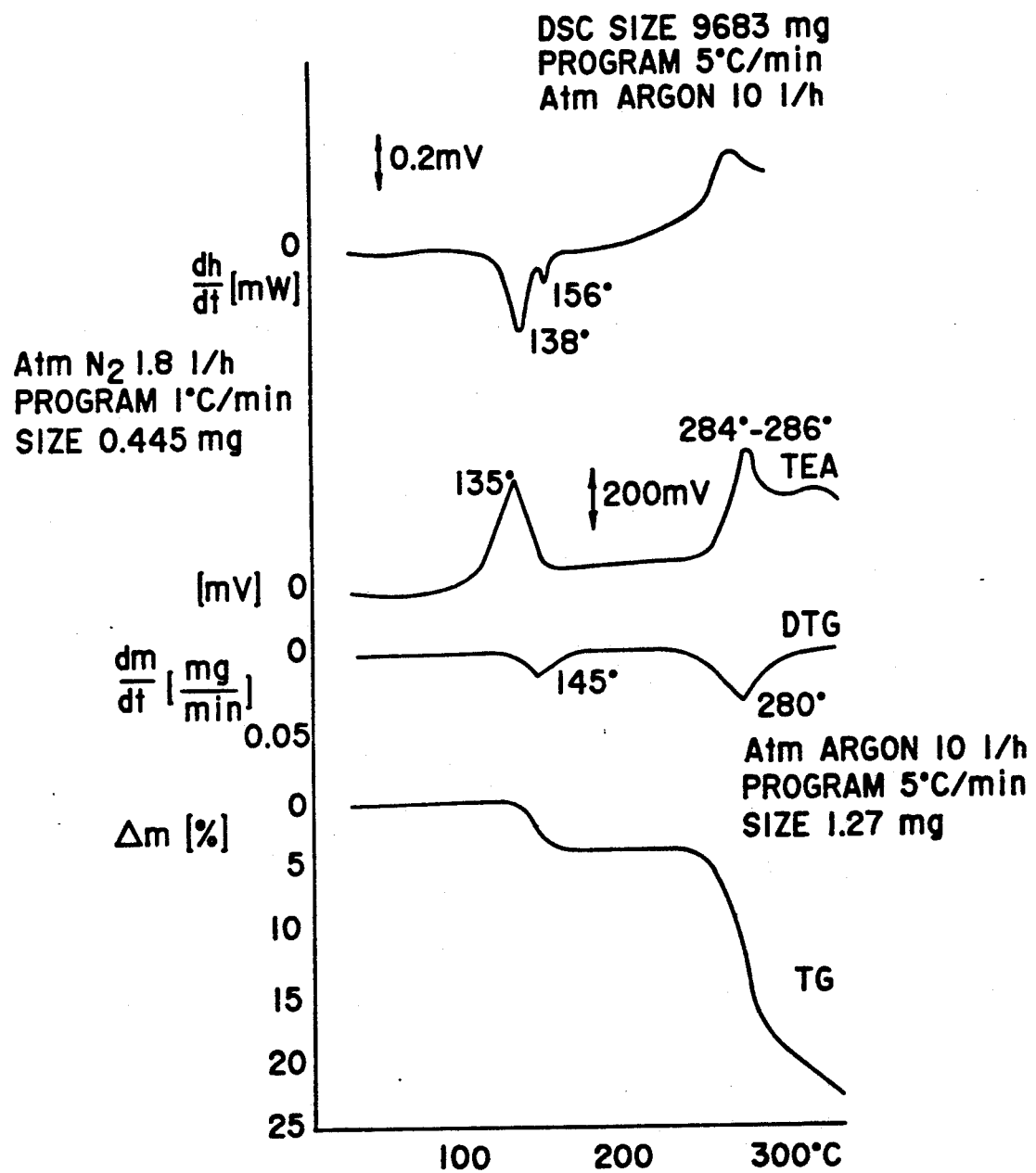
FIG. 4 shows thermoanalytical curves of Silybinin
Figure 5:
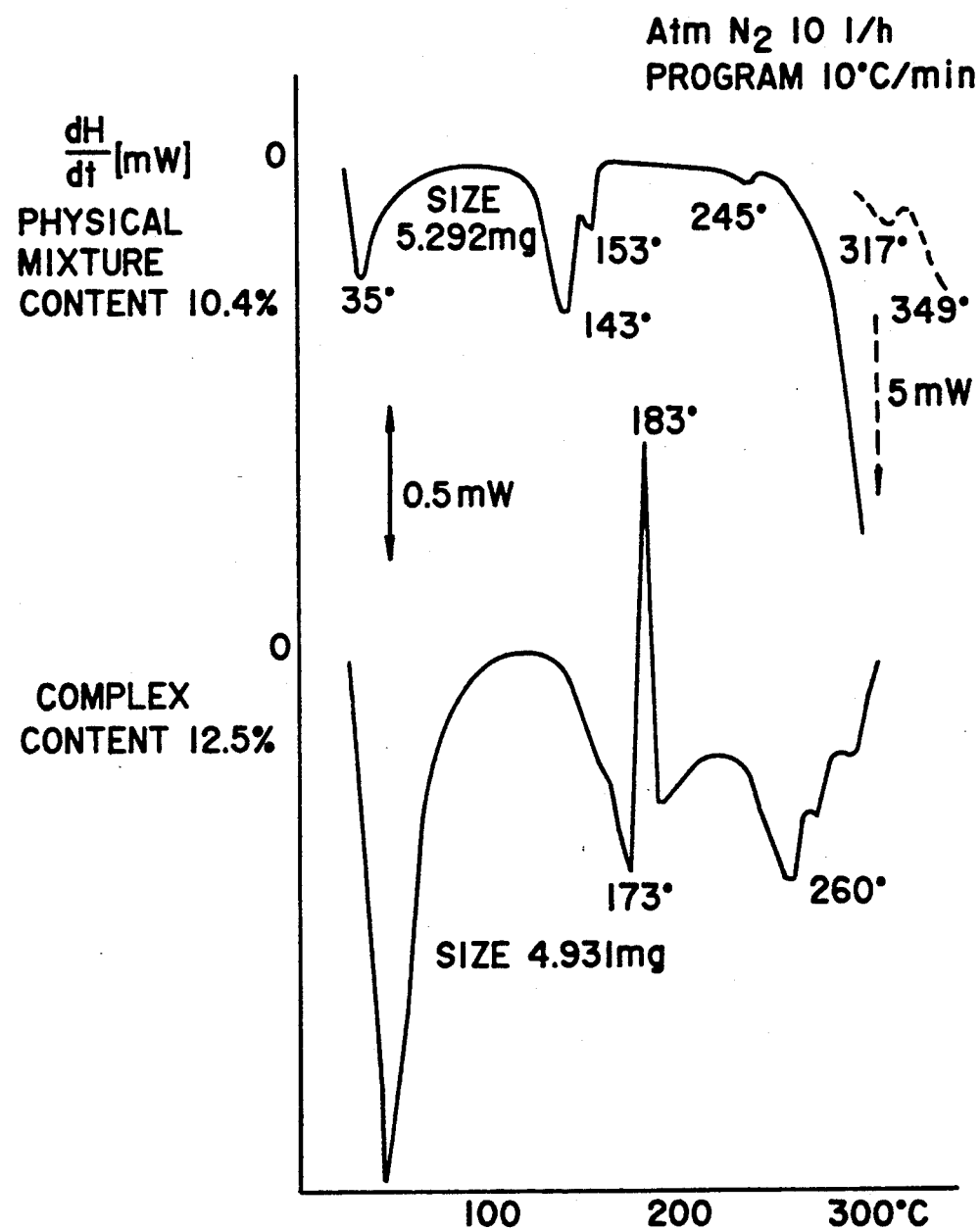
FIG. 5 shows DSC curves of the complex of Example 7 and of a physical admixture of Silybinin and DIMEB
Figure 6:
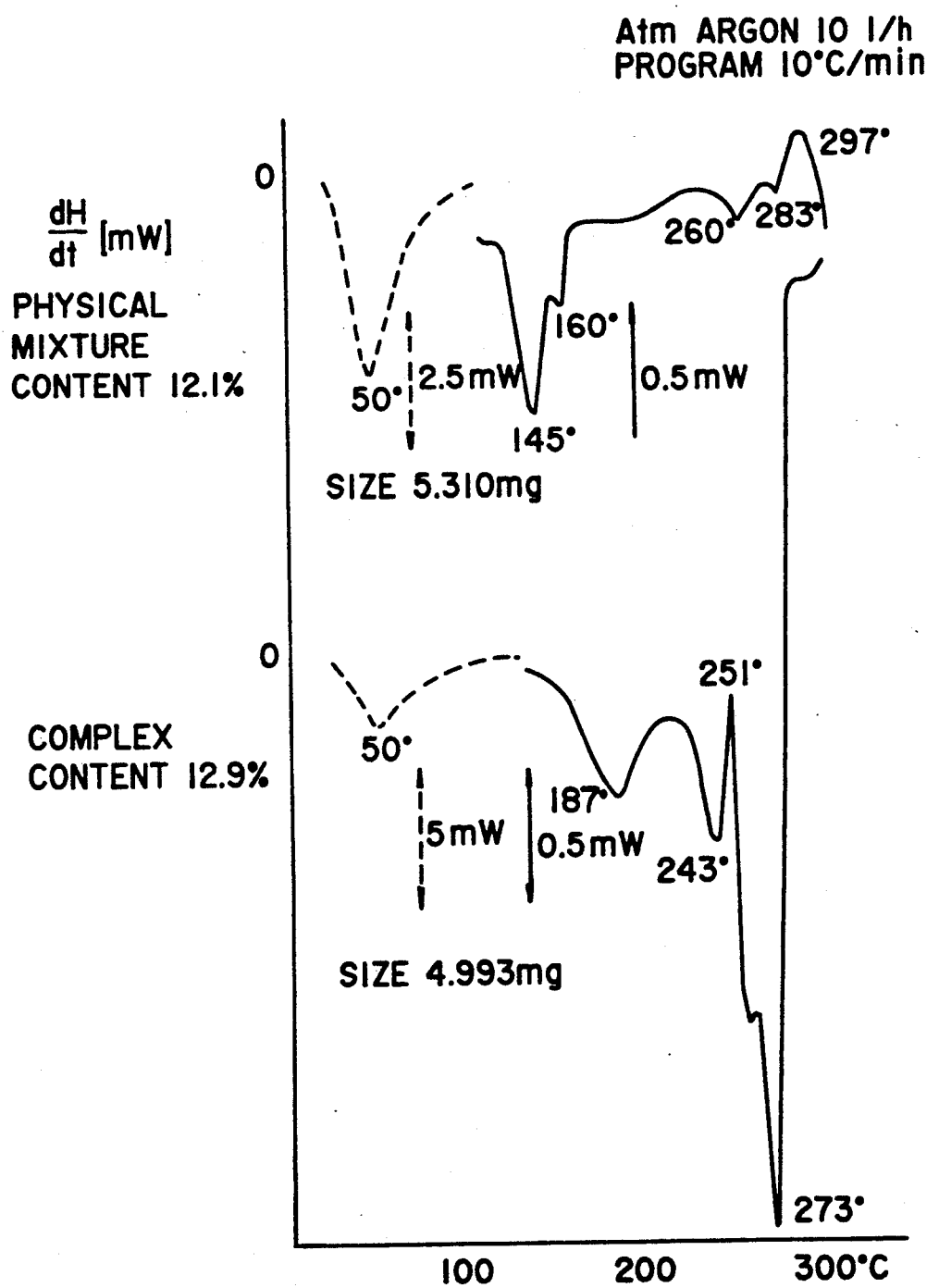
FIG. 6 shows DSC curves of the complex of Example 8 and of physical admixture of Silybinin and HPβCD

DSC curves of Silybinin (FIG. 4) indicates that the decomposition of the drug begins at about 130° C. and up to 160° C. about 4–5% loss of weight is observed. The second decomposition step of the drug starts above 250° C. in the region of the cyclodextrin decomposition. The decomposition step at the lower temperature is suitable to differentiate the complexed and the non-complexed products. DSC curves of the complexes (FIGS. 5,6) show that the decomposition of Silybinin is observed at higher temperature only at about 175°–180° C.

Solubility Properties of the Complexes of Examples 7 and 8.

Figure 7:
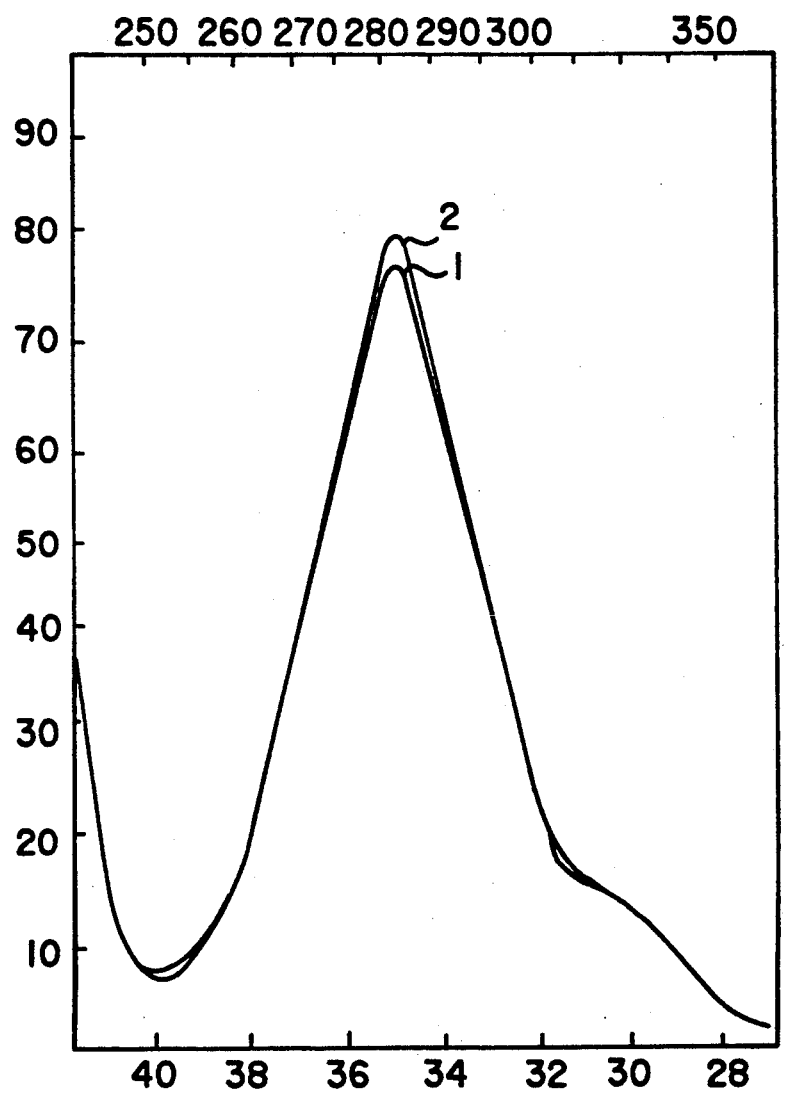
FIG. 7 is the UV-spectrum of the complex of Example 7 (1) and Example 8 (2)

Milligrams 250 of DIMEB and HPβCD complex can easily be dissolved in 2 ml of distilled water and in pH 1.4 hydrocloric acid resulting in a clear solution. The UV-spectra of the aqueous solutions—recorded after 1:750 dilution with 50% (v/v) ethanol—show undoubtly that Silybinin is included both in DIMEB and HPβCD in unionized form (FIG. 7).

The pH of the aqueous solutions:
DIMEB complex: 3.3
HPβCD complex: 3.4

After one day following the dissolution no precipitation was observed in the DIMEB-complex solution. DIMEB complex solution remained clear more than 10 days of storage. UV-spectra recorded remained unaltered indicating the good stability of Silybinin complexes in solutions.

EXAMPLE 9

Pharmaceutical Composition Containing the Silybinin: β-cyclodextrin Inclusion Complex (Molar Ratio=1:2)

Silybinin to titre: 40.0 mg
β-cyclodextrin: 164.7 mg
Pharmacoat 606: 10.0 mg
Sodium laurylsulphate: 15.0 mg
Polyethyleneglycol: 15.0 mg
Lactose: 103.8 mg
Magnesium stearate: 1.5 mg
Hard gelatin capsules of size "1".

Silybinin and β-cyclodextrin are mixed in a water-/methyl alcohol solution (7:3) at 45° C. for two hours, then methyl alcohol is evaporated and the product lyophilized. It is analyzed by X-ray (PW1800 Philips diffractometer for powder; CuKα radiation; Ni filter; Kv40mA20) and it shows a diffractogram which does not correspond to the simple addition of the β-cyclodextrin and Silybinin spectra, but where are present some novel signals (such as for example 2θ=43.3) while there are missing some peaks which on the are characteristic of the mechanical mixture of the two components (2θ=24.5; 14.6; 32; 22.7). That confirms the formation of the inclusion complex.

The lyophilized product is kneaded with a 2% w/v Pharmacoat 606 in methylene chloride/ethyl alcohol (9:1) solution. The so obtained mixture is granulated on a 1.2 mm mesh sieve, dried and scraped on a 0.840 mm mesh sieve. The granulated product is operculated in capsules of size "1".

The binding solution may be replaced by a polyvinylpyrrolidone solution in ethyl alcohol/water or by an aqueous gelatin solution. The polyethyleneglycol molecular weight may vary from 1,500 to 10,000.

EXAMPLE 10

Pharmaceutical Composition Containing the Silybinin: β-cyclodextrin Inclusion Complex (molar ratio=1:2.75)

Silybinin: β-cyclodextrin complex: 330 mg.
Pharmacoat 606: 10.0 mg
Sodium laurylsuphate: 15.0 mg
Polyethyleneglycol: 15.0 mg
Lactose: 103.8 mg
Magnesium stearate: 1.5 mg The inclusion complex is kneaded with a 2% w/v Pharmacoat 606 in methylene chloride/ethyl alcohol solution. The so obtained mixture is granulated on a 1.2 mm mesh sieve, dried and scraped on a 0.840 mm mesh sieve. The granulated product is operculated in capsules of size "1".

The binding solution may be replaced by a polyvinylpyrrolidone solution in ethyl alcohol/water or by an aqueous gelatin solution. The polyethyleneglycol molecular weight may vary from 1,500 to 10,000.

EXAMPLE 11

Pharmaceutical Composition Containing the Silybinin: γ-cyclodextrin Inclusion Complex (Molar Ratio 1:2)

Operation is carried out as described in Example 9 using:
Silybinin to titre: 40.0 mg
γ-cyclodextrin: 188.1 mg

EXAMPLE 12

Pharmaceutical Composition Containing the Silybinin: β-cyclodextrin Inclusion Complex (Molar Ratio 1:4)

Operation is carried out as described in Example 9 using:
Silybinin to titre: 40.0 mg
β-Cyclodextrin: 328.4 mg
Pharmacoat 606: 10.0 mg
Sodium laurylsulphate: 15.0 mg
Polyethyleneglycol: 15.0 mg
Lactose: 129.1 mg
Magnesium stearate: 1.5 mg
Hard gelatin capsules of size "0".

EXAMPLE 13

Pharmaceutical Composition Containing the Silybinin: DIMEB Inclusion Complex (Molar Ratio 1:2)

Operation is carried out as described in Example 9 using:
Silybinin to titre: 40.0 mg
DIMEB: 220.77 mg The absorption of the complexes of the invention has been evaluated by orally administering an aqueous solution of the composition under examination and measuring by HPLC the Silybinin bile levels. This test has been preferred because it is well known that drugs of the Silymarin kind reach in the bile the highest concentration.

The experiments have been carried out on Wistar rats weighing 180–200 g to which the compositions under examination were administered by gastric intubation. The animals were kept on an empty stomach for 16 hours. The composition to be tested was dissolved in water containing 10% of gum Arabic and were prepared solutions so that each animal was administered-,each time with an amount of 5 ml/kg of said solution.

Immediately after the treatment the animals were anaesthetized and operated to check the coledocous duct. A small tube was inserted therein and the bile was collected over a period of 24 hours.

For the analytical determination 1 ml bile was treated as described in the following publication: D. Lorenz et al, Pharmacokinetic Studies with Silymarin in Human Serum and Bile—Meth. and Find.Exptl.Clin.Pharmacol.6(10) 655–661 (1984).

The data obtained from the tests are listed in the following Table 2 where:

in test A, there were administered 20 mg/kg of Silymarin, according to a known commercial formulation which corresponds to 8 mg/kg of pure Silybinin, in test B, there were administered 8.79 mg/kg of Silybinin having a HPLC titre of 91%, which corresponds to 8 mg/kg of pure Silybinin, used such as without excipients, in test C, there were administered 29.2 mg/kg of the Silybin: β-cyclodextrin inclusion complex, described in Example 1, which possess a HPLC, titre in Silybinin 27.4% corresponding to 8 mg/kg of pure Silybinin.

TABLE 2

| Product | Number of animals | Bile Volume | Bile 0–24 hr mcg/ml | 0–24 hr mcg/rat | % excreted Silybinin |
|---|---|---|---|---|---|
| Silybinin (Test B) | 12 | 12.2 | 1.0 | 11.9 | 0.6 |
| Silybinin (Test A) | 15 | 11.4 | 6.4 | 73.8 | 2.7 |
| Complex of Ex. 1 (Test C) | 14 | 14.3 | 17.6 | 256.6 | 11.7 |

The average volume of bile produced in 24 hours by a non-treated rat is 13.4 ml.

The evaluation of the data obtained shows that the administration of the composition containing as active ingredient the inclusion complex according to the invention allows to obtain, using the same amount of active ingredient in all the tests, concentration levels in Silybinin more than doubled when compared to those obtained in test A and nearly twenty times those obtained in test B.

In a further experiment the resorption of Silymarin, Silybinin and of the complex of Example 6 was evaluated. For this purpose the excretion of Silybinin in the rat bile was determined in a conventional model experiment. Anesthetized male Wistar SPF rats kept under conventional conditions, were cannulated at the ductus choledochus. After intragastric administration of the test compound (5 mg Silybinin/kg) the bile fluid was collected for 5hr. The Silybinin content in the bile fluid was determined by quantitative thin layer chromatography.

The results were as follows:
% excretion of Silybinin in rat bile:
Silymarin: 11.9%[1]
Silybinin: 0.21%[2]
Complex: 17.3%[3] [1] Average calculated from 5 experiments [2] Average calculated from 10 experiments [3] Average calculated from 7 experiments The above data show that the complex is more and easier absorbed than Silybinin and Silymarin.

We claim:

1. An inclusion complex of silybinin and a cyclodextrin selected from the group consisting of α-cyclodextrin, β-cyclodextrin, γ-cyclodextrin and derivatives thereof, wherein the molar ratio of silybinin to the cyclodextrin is 1:1 to 1:4.

2. An inclusion complex according to claim 1, wherein the cyclodextrin in β-cyclodextrin.

3. An inclusion complex according to claim 1, wherein the cyclodextrin is eptakis-2,6-O-dimethyl-β-cyclodextrin, eptakis-2,3,6-O-trimethyl-β-cyclodextrin or 0eptakis-2,3,6-O-trimethyl-β-cyclodextrin or 0-hydroxypropyl-β-cyclodextrin.

4. An inclusion complex according to claim 1, wherein the molar ratio of silybinin to the cyclodextrin is 1:2.75.

5. An inclusion complex according to claim 1, wherein the molar ratio of silybinin to the cyclodextrin is 1:2.

6. A process for preparing an inclusion complex of silybinin and a cyclodextrin selected from the group consisting of α-cyclodextrin, β-cyclodextrin, γ-cyclodextrin and derivatives thereof, which comprises dissolving silybinin and the cyclodextrin in water at a pH above 7, adding an acid to lower the pH of the solution to below 7, and isolating the thus formed inclusion complex.

7. A process for preparing an inclusion complex of silybinin and a cyclodextrin selected from the group consisting of α-cyclodextrin, β-cyclodextrin, γ-cyclodextrin and derivatives thereof, which comprises suspending silybinin in water, adding a base to dissolve the silybinin, adding the cyclodextrin to the solution of silybinin, adding an acid to the solution to lower the pH to below 7, and isolating the thus formed inclusion complex.

8. A pharmaceutical composition comprising an antihepatotoxic effective amount of at least one inclusion complex according to claim 1 in combination with a pharmaceutically acceptable carrier or adjuvant.

9. A pharmaceutical composition comprising an antihepatotoxic effective amount of at least one inclusion complex according to claim 2 in combination with a pharmaceutically carrier or adjuvant.

10. A pharmaceutical composition comprising an antihepatotoxic effective amount of at least one inclusion complex according to claim 3 in combination with a pharmaceutically carrier or adjuvant.

* * * * *

UNITED STATES PATENT AND TRADEMARK OFFICE
CERTIFICATE OF CORRECTION

PATENT NO. : 5,198,430
DATED : March 30, 1993
INVENTOR(S) : Umberto VALCAVI et al.

It is certified that error appears in the above-identified patent and that said Letters Patent is hereby corrected as shown below:

Column 8, line 58, delete "or Oeptakis-2,3,6-O-trimethy-ß-cyclodextrin".

Signed and Sealed this

Fifteenth Day of February, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,198,430
DATED : March 30, 1993
INVENTOR(S) : Umberto Valcavi, et. al.

It is certified that error appears in the above-indentified patent and that said Letters Patent is hereby corrected as shown below:

On the Title page, item [73], Assignee: should read--Instituto Biochimico Italiano Giovanni Lorenzini SpA, Milan, Italy; and Madaus AG, Koln, Federal Republic of Germany--.

Signed and Sealed this

Twenty-sixth Day of April, 1994

Attest:

BRUCE LEHMAN

*Attesting Officer*   *Commissioner of Patents and Trademarks*